United States Patent [19]

Ainger, III

[11] Patent Number: 5,169,568
[45] Date of Patent: Dec. 8, 1992

[54] METHOD FOR CASTING A HOUSING AROUND AN ENDOSCOPE FRAME

[76] Inventor: Raymond Ainger, III, 1103 Hope St., Stamford, Conn. 06907

[21] Appl. No.: 632,054

[22] Filed: Dec. 21, 1990

[51] Int. Cl.$^5$ .................... B29D 11/00; B29C 39/10
[52] U.S. Cl. ...................................... 264/1.5; 128/7; 264/263; 264/277
[58] Field of Search ................. 264/1.5, 263, 277; 128/7, 662.06

[56] References Cited

U.S. PATENT DOCUMENTS

| 4,541,433 | 9/1985 | Bandino | 128/662.06 |
| 4,802,461 | 2/1989 | Cho | 128/7 |
| 4,899,732 | 2/1990 | Cohen | 128/6 |
| 4,911,148 | 3/1990 | Sosnowski et al. | 128/7 |
| 4,986,258 | 1/1991 | Cho | 128/7 |

FOREIGN PATENT DOCUMENTS 2-95811  4/1990  Japan .................... 264/1.5

Primary Examiner—James Lowe

[57] ABSTRACT

A method for casting a housing around an endoscope frame is shown. The method includes the step of assembling an endoscope frame comprising a proximal end of an elongated shaft having a first working channel, a second working channel, a fiber optical image bundle channel, and fiber optic light carrying member. Each of the working channels and the fiber optic light carrying member extend in a predetermined direction from the elongated shaft to a preselected location wherein each of the working channels are terminated in an input opening member. The fiber optic image bundle terminates in a viewing member. The fiber optic light carrying member terminates in a light connecting member. The method then comprises the step of casting with a curable material a housing having a predetermined shape and exterior outer surface around the endoscope frame including the proximal end of an elongated shaft, a first working channel, a second working channel, a fiber optic image bundle channel and a fiber optic light carrying member such that the input opening member of each working channel and a light connecting member of the fiber optic light carrying member extend through the exterior outer surface at separate and distinct locations which are positioned in a spaced relationship from the exterior outer surface and with a viewing member for terminating the fiber optic image bundle positioned interiorly within the housing, all of which form a fluid tight seal with the housing.

13 Claims, 4 Drawing Sheets

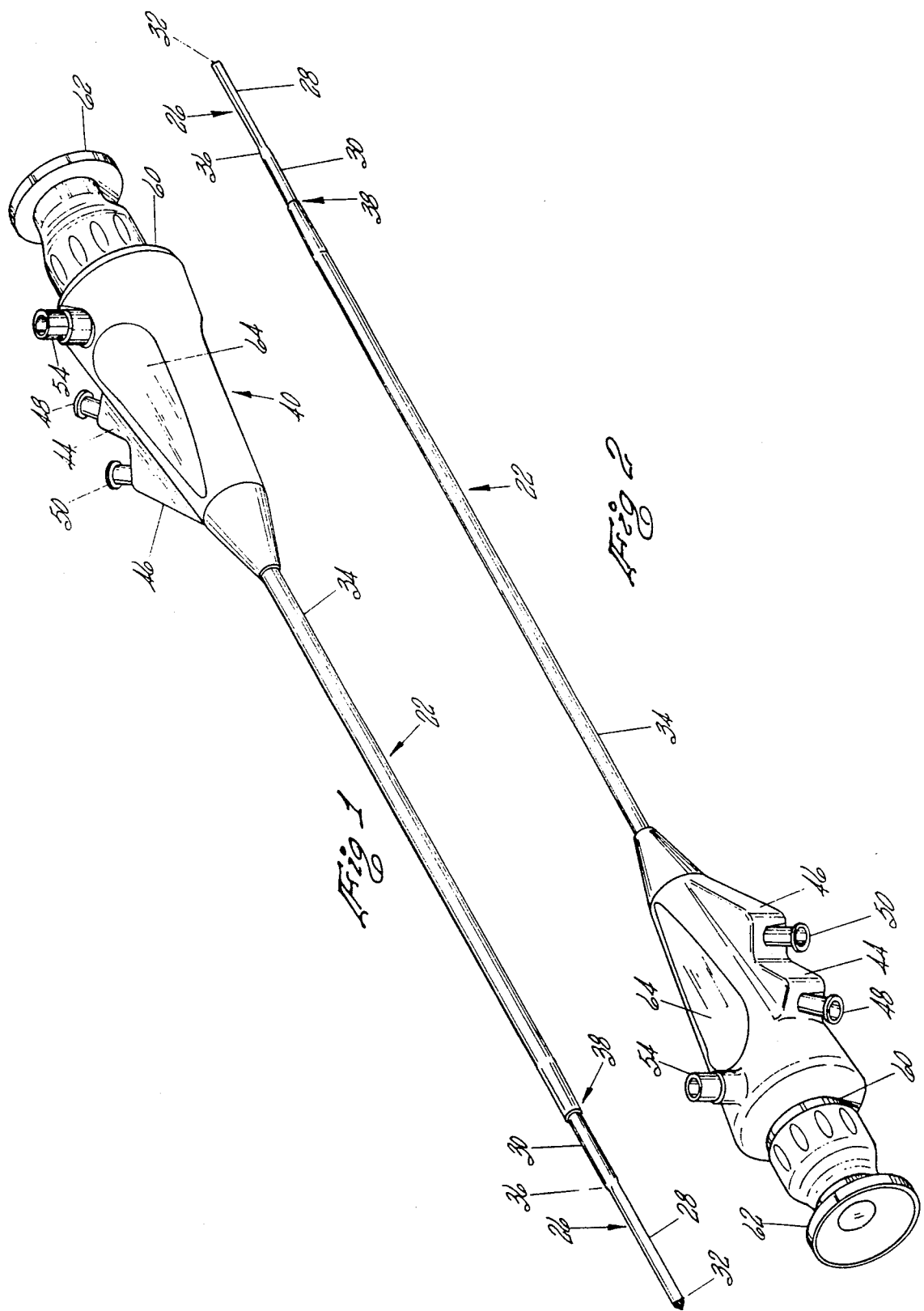

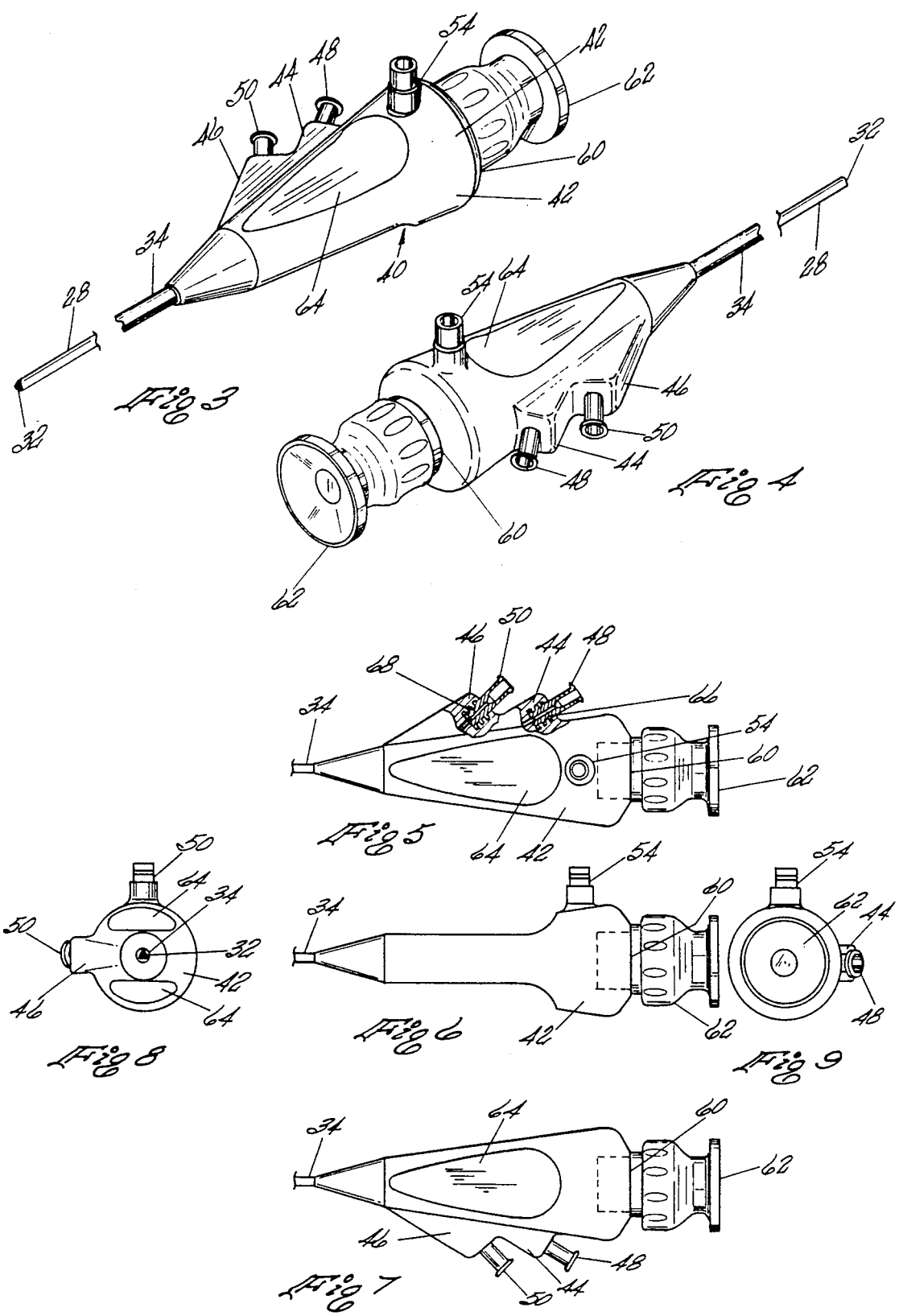

METHOD FOR CASTING A HOUSING AROUND AN ENDOSCOPE FRAME

BACKGROUND OF THE INVENTION

1. Field of Invention

This invention relates to an endoscope which is used for performing a procedure inside a body cavity or passageway and is more particularly directed towards an endoscope in the form of a mini-rigid ureteroscope which is used to perform medical procedures classified as diagnostic endoscopic examinations and therapeutic endoscopic procedures. The mini-rigid ureteroscope has an elongated shaft including a first elongated sheath tube having a deflectable distal section and a second elongated semi-rigid sheath tube which encloses a major portion of the first elongated sheath tube. The deflectable distal section extends beyond the distal end of the second semi-rigid elongated sheath tube. The endoscope is adapted to be inserted into the ureter of a patient for performing a medical examination and/or procedure within the ureter. This invention also relates to a method for casting a housing of a predetermined shape around an endoscope frame to form a fluid tight seal around working channels, viewing means for a fiber optic image bundle channel having a fiber optic image bundle and fiber optic light carrying means, all forming a part of the endoscope. This invention also relates to an image means for an instrument having a rod-like image transferring means wherein the rod-like image transferring means is rigidly attached to the instrument at a selected location along its length and wherein a slidably supporting means slidably supports the rod-like image transferring means at least at one location along the length to permit relative movement between the rod-like image transferring means and the instrument.

A method for casting a housing around an endoscope frame is also disclosed. The method includes the step of casting with a curable material a housing having a predetermined shape and an exterior outer surface wherein the housing is cast around an endoscope frame which includes a proximal end of an elongated shaft, a first working channel, a second working channel, a fiber optic image bundle channel and a fiber optic light carrying means and appropriate termination or connector for such elements.

2. Description of the Prior Art

Endoscopes with an elongated shaft for viewing a body canal and for performing a surgical procedure within the body canal are known in the art. Typical of these devices is an endoscope with tapered shaft of U.S. Pat. No. 4,986,258 which replaced withdrawn U.S. Pat. No. 4,961,414 and a rigid endoscope with flexible tip covered in U.S. Pat. No. 4,802,461. A mini-scope catheter adapted to perform diagnostic procedures in smaller body parts, such as, for example, the bile duct or interior of the gall bladder, and which is constructed to allow the operator to control the deflection of a catheter tip is disclosed in U.S. Pat. No. 4,899,732.

The endoscope with tapered shaft disclosed in U.S. Pat. No. 4,986,258 utilizes a plurality of stages which are either step tapered or uniformly tapered to provide a distal section, a central section and a proximal section. The various stages or sections may be formed by a plurality of coaxially aligned tubes of decreasing diameters or could be formed of a single elongated shaft which is machined to provide the desired tapered surface along its length with the distal end having the smaller geometrical dimension. The transition zones between the three stages of the endoscope occur at about each third of the length and the transition for a two stage endoscope is approximately at the one half length or mid-point location.

U.S. Pat. No. 4,986,258 discloses that the final stage may include a flexible tip portion at the distal end of the shaft which is controllable from an endoscope handle. A mechanism for deflecting the flexible tip of a rigid endoscope, which could be used for such a flexible tip in an endoscope with taper shaft, is disclosed in U.S. Pat. No. 4,802,461 noted above. The tip end of the tube is barely flexible, relative to the length of the tube. Wires connected to opposite ends of the flexible tip provide the user with the means to control the flexing of the distal tip.

Also, U.S. Pat. No. 4,899,732 discloses a catheter, which has a deflectable catheter tip and which includes at least one lumen, which can be used to receive a stylet or to pass a contrast medium. In addition, the mini-catheter includes two optical filament channels, one for carrying light to the distal end and the other for transmitting an optical image to the proximal end of the catheter.

The cross-sections of each the above described endoscopes and mini-scope are generally circular in shape and provide a distal tip which can be utilized to be inserted in to the orifice of the body canal or duct, as the case may be.

It is also known in the art to utilize a ureteroscope to perform certain procedures in the urethra, bladder, ureter or kidney. Generally, ureteroscopes are used to view the ureter or perform procedures in the ureter. As such, the endoscopes include a semi-rigid elongated shaft to enable the urologist or user to insert the distal tip through the urethra orifice and to advance the same through the bladder and through the intra-mural ureter to some location in the ureter.

Surgical procedures may be performed within the urinary system such as destroying and/or removing bladder stones, ureteral stones, kidney stones or examining calyces of the kidney. It is also known to use mechanical accessories or working tools such as lithotriptors, electrohydraulic probes, stone baskets or laser fiberguides to break up a stone and to perform other known procedures. The flexibility of the tip and the length of the semirigid section are important features of a ureteroscope in the urology field. The reason that the above features are important is that the anatomical path of the ureter between the bladder and the kidney is not a straight line and, in some cases, can be quite torturous.

Ureteroscope sheaths for performing procedures in the ureter are known in the art. Typical of such ureteroscope sheaths are devices offered for sale and sold by the CIRCON ACMI Division of Circon Corporation, which are identified as Catalog Numbers HUS-10S and HUS-10L. These Catalog Number devices are basically the same ureteroscope sheath with Catalog Number HUS-10L having a longer elongated shaft to enable the urologist to advance the ureteroscope sheath further into the ureter.

The Catalog Numbers HUS-10S and HUS-10L ureteroscopes are constructed to have a semi-rigid section which is operatively attached to a relatively rigid proximal section forming a two diameter stepped elongated shaft. The two sections are joined with the proximal end of the semi-rigid section mechanically attached to the distal end of the relatively rigid proximal section at a point approximately midway along the elongated shaft. A tapered joint or a step-tapered joint is provided depending on the manufacturing assembly of the ureteroscope sheath. The degree of taper at the transitional zone or joint area is controlled by metal polishing and other known manufacturing techniques.

Each of the above known endoscopes, flexible mini-catheters and the ureteroscope sheaths have at least one working channel. The endoscopes and mini-catheter include a fiber optic image bundle. A fiber optic light carrying means may be dispersed around the working channels and fiber optic image bundle channel or may be located in a separate dedicated fiber optic light bundle channel.

None of the known prior art devices disclose an endoscope having an elongated shaft wherein one transitional zone exists between a semi-rigid proximal section and deflectable distal section wherein the transitional zone is located generally in the distal area, such as the first quarter length, of the elongated shaft, as measured from the distal tip. Further, the endoscope of the present invention may have the flexible distal section thereof terminate in a distal portion which has a geometrically shaped cross-sectional area having at least one protuberance. In the preferred embodiment, the distal section is triangular shaped and has a plurality of working channels, which may be of the same or different sizes and shapes, a fiber optic image bundle channel having a fiber optic image bundle and a fiber optic light carrying means. The endoscope of the present invention may be used to view the interior of a cavity or passageway and the working channels may be utilized for performing procedures within the cavity or passageway.

As the state-of-the-art advances in the ureteroscopy field, it has developed that endoscopes having a shorter elongated shaft wherein the distal section of the shaft is flexible and the proximal section of the shaft is semi-rigid are preferred. Specifically, such endoscopes are preferred for performing visual examinations within the urinary system and for performing various procedures and providing treatment for diseases of the urinary tract. Typical of articles which disclose the use of a rigid endoscope in the management of ureteral diseases are: (1) URETEROSCOPE WITH RIGID INSTRUMENTS IN THE MANAGEMENT OF DISTAL URETERAL DISEASE by Tobias M. Goodman which appeared in the Journal of Urology, August, 1984, Volume 132, at pages 250 (The "Goodman Publication"); and (2) URETERAL LASER LITHOTRIPSY USING THE PULSOLITH by Demetrius H. Bagley, M.D., Michael Grasso, M.D., Mohammed Shalaby, M.D. and Magdy Abass El-Akkad, M.D. which appeared in the Journal of Endourology, Volume 3, Nov. 1, 1989, at Pages 91-98 (The "Bagley et al. Publication").

The Goodman Publication discloses that the rigid ureteroscope allows for ureteroscopic manipulation of the ureter because of the anatomical arrangement of the body. Ureteroscopy with a rigid instrument usually is performed with the patient under anesthesia. The Goodman Publication also describes the procedure is performed by introducing the distal tip of the rigid ureteroscope into the urethra and passing the instrument transurethrally. The ureteroscope is then introduced into the ureteral orifice. Usually, this is done visually through an eyepiece or by observing a video image developed by a video camera attached to the ureteroscope. The Goodman Publication specifically discloses the necessity of having the exterior of the sheath of the ureteroscope very smooth and of small caliber such that the ureter will adjust to the increasing size of the instrument as it is transversed throughout the ureter. The procedure described in the Goodman Publication demonstrates the applicability of ureteroscopy to every day problems encountered by a urologist.

The Bagley et al. Publication discloses use of a Pulsolith TM Laser as a highly effective tool for the destruction of ureteral calculi including those of calcium oxalate monohydrate. The small flexible fibers required to be used with the laser are delivered with rigid or flexible endoscopes throughout the upper urinary tract. The Bagley et al. Publication discloses that the endoscopic access to the distal ureteral calculi with rigid instruments is extremely successful. However, when calculi are located in mid or upper ureteral locations, flexible ureteroscopy is generally more successful in accessing those more proximal locations.

SUMMARY OF THE INVENTION

The present invention discloses a novel, unique and improved endoscope which is capable of being used in ureteroscopy in the management of ureteral disease. In the preferred embodiment, the endoscope is a mini-rigid ureteroscope which includes an elongated shaft wherein the shaft includes a first elongated sheath tube having a selected length and includes a deflectable distal section. The deflectable distal section has at its distal end a triangular cross-sectional area of a selected geometrical dimension which terminates in a distal tip. The elongated shaft includes a second semi-rigid elongated sheath tube having a predetermined length which is greater than one-half of the selected length and less than the selected length. This essentially places the transition zone between the sheath tubes in the distal area of the endoscope. The second semi-rigid elongated shaft is positioned over and encloses the proximal section of the first elongated sheath tube with a deflectable distal section extending beyond the second semi-rigid elongated sheath tube. The second semi-rigid elongated sheath tube has a cross-sectional shape sufficient to pass the first elongated sheath tube therethrough.

A method is shown for casting a housing around an endoscope frame. The method includes the step of assembling an endoscope frame comprising a proximal end of an elongated shaft having a first working channel, a second working channel, a fiber optic image bundle channel and fiber optic light carrying means which extends into and which is interspersed within the elongated shaft and around the first working channel, the second working channel and the fiber optic image bundle channel. Each of the working channels and the fiber optic light carrying means extend in a predetermined direction from the distal end of the elongated shaft to a preselected location wherein each of the channels are terminated in an input opening means, wherein the fiber optic image bundle terminates in a viewing means and wherein the fiber optic light carrying means terminates in a light connecting means.

The next step is casting with a curable material a housing having a predetermined shape and exterior outer surface around the endoscope frame including the proximal end of the elongated shaft, the first working channel, the second working channel, the fiber optic image bundle channel and the fiber optic light carrying means such that the input opening means of each working channel and the light connecting means of the fiber optic light carrying means extend through the exterior outer surface of the housing at separate and distinct locations which are positioned in a spaced relationship from the exterior outer surface and with the viewing means positioned within the housing, all forming a liquid tight seal with the housing.

An imaging means for an instrument is disclosed. The imaging means includes means defining an image channel within the instrument. The imaging means also includes means for defining a rod-like image transferring means having a distal end and a proximal end for transmitting an optical image within the instrument. The rod-like image transferring means is located within the image channel such that the distal end of the rod-like image transferring means is located at one end of the instrument and the proximal end of the rod-like image transferring means is located at an opposed second end of the instrument. The image means also includes means for defining at one end of the instrument an objective lens which is spaced from the distal end of the rod-like image transferring means for focusing an optical image onto an orifice of the rod-like image transferring means at the distal end thereof. The image means further includes means for rigidly attaching the rod-like image transferring means at a selected location along its length and for slidably supporting the rod-like image transferring means at least at one location along its length.

The rigid endoscopes known in the prior art, such as the endoscope described in U.S. Pat. No. 4,986,258 have certain disadvantages. The structure of the elongated shaft is such that the transitional zones which define the joint or joints between stages result in reduced mechanical stiffness at the joints. The joints or transition zones of the prior art endoscope are generally located equidistantly along the elongated shaft. The joints appear to provide discrete stress points which during deflection and rotation which occurs during the maneuvering of the endoscope during a procedure, could result in the elongated shaft becoming bent or actually breaking away during the procedure.

Also, endoscopes and ureteroscopes known in the art have two distinct sections in terms of a distal section and a proximal section, and these distinct sections are joined together mechanically at a central joint such that the transition zone is located centrally along the shaft. The central joint or central transition zone is typically a weak or stress point such that under flexing or rotational forces, a bending or breaking away or separating of the distal section from the proximal section could occur during a procedure.

One advantage of the present invention is that the single transition zone between the sheath tube is, in the preferred embodiment, tapered as opposed to being stepped. This feature substantially reduces stress concentrations which in turn, increases the durability of the shaft to bending metal fatigue.

Another advantage of the present invention is that the ureteroscope has an integrated elongated shaft which is formed from two coaxially aligned elongated sheath tubes wherein the first elongated sheath tube has a selected length as measured from its proximal end to its distal end. The second elongated sheath tube is shorter in length than the selected length of the first elongated sheath tube. The length of the second semi-rigid elongated sheath tube is greater than one-half the length of the first elongated sheath tube and less than the selected length. This results in defining a transitional zone that is the area, section, location or point where the second elongated semi-rigid sheath tube encloses, is contiguous to and supports the first elongated sheath tube. As such, the deflectable section extends, on one hand, a sufficient distance beyond the distal end of the second semi-rigid elongated sheath tube to provide the desired flexibility, and, on the other hand, the second semi-rigid sheath tube provides sufficient rigidity throughout the length of the elongated shaft to inhibit permanent bending or separation.

Another advantage of the present invention is that the first elongated sheath tube includes a deflectable distal section which extends beyond the second semi-rigid elongated sheath tube and wherein the distal portion has a geometrically shaped cross-sectional area having at least one protuberance. By controlling the structure of the geometrically shaped cross-sectional area to be essentially non-circular, the flexibility of the distal section can be fabricated to essentially have an easy flexing direction and a more rigid flexing direction. For example, the geometrical shape of the distal section may be triangular shaped, tear drop shaped (e.g. two sides of a triangle being straight sides with the third side being a sector of a circle) or elliptical shaped having a major and minor axis.

Another advantage of the present invention is that the distal section, in the preferred embodiment, terminates at a distal tip having a substantially triangular cross-sectional area including a smooth triangular shaped perimeter. A triangular shape provides the smallest perimeter around the various working and optical channels and thereby causes the least dilation of the ureter as the distal section of the ureteroscope gently passes through the ureter. In the preferred embodiment, the endoscope includes two working channels which preferably includes a 3.4 French channel and a 2.3 French channel. Each of the working channels can be utilized in the ureteroscopy procedure.

Another advantage of the present invention is that the distal tip can be beveled and has a perimeter, in the preferred embodiment, in the order of about 7 French. A 7 French distal tip enables the surgeon to ease the distal tip into the ureteral orifice with little or no dilation.

Another advantage of the present invention is that the endoscope when used in a ureteroscopy procedure, reduces operating time and patient trauma. Certain endoscopic procedures can be performed with no dilation or without the use of general anesthesia due to the fact that the small distal tip can be easily inserted through the urethral orifice without significant patient trauma.

Another advantage of the present invention is that the endoscope can be utilized in a procedure or method for performing a procedure in a cavity or passageway in a human body. The method would generally include the step of providing an endoscope including an elongated shaft having a first elongated sheath tube and a second semi-rigid elongated sheath tube, inserting the substantially triangular shaped flexible distal section of the elongated shaft into the cavity such as for example, the urethral orifice, followed by the second semi-rigid elongated sheath tube which passes into the cavity or passageway and viewing from the proximal section of the first elongated sheath tube the cavity or passageway through one channel in the endoscope. The endoscope disclosed herein includes a first working channel and a second working channel and the method further comprises the step of passing a working tool through at least one of the first working channel or second working channel to perform a procedure in a cavity or passageway.

Another advantage of the present invention is that the endoscope includes means defining a fiber optic image bundle channel which encloses and receives a fiber optic image bundle. A fiber optic light carrying means or bundle is likewise located within the endoscope and is interspersed around the working channels and the fiber optic image bundle channel to provide a means for carrying light to the distal tip of the endoscope.

Another advantage of the present invention is that an optical wedge can be located at the distal tip of the deflectable section to provide a direction of view for the endoscope of about 5 degrees to about 10 degrees when viewed under water.

Another advantage of the present invention is that the interior walls forming the first working channel and the second working channel can be coated with a material having a reduced coefficient of friction to facilitate easy passage of and use of accessories in the working channel.

Another advantage of the present invention is that an imaging means for an instrument is disclosed wherein a rod-like image transferring means, such as for example, a fiber optic image bundle channel which contains a fused fiber optic image bundle which is utilized for transmitting an optical image. The distal end and the proximal end of the rod-like image transferring means, e.g. a fused fiber optic bundle, can be supported by a first supporting means and a second supporting means, respectably. Depending on the structure of the endoscope, the distal end of the rod-like image transferring means, such as the fused fiber optic image bundle, can be rigidly attached to the first supporting means which spaces the face of the fused fiber optic image bundle a predetermined distance from the objective lens to enable an image to be focused onto the face of the distal end of the fused fiber optic image bundle. The second supporting means then permits relative movement between the fused fiber optic image bundle and the instrument. This movement, that is the sliding relationship between the fused fiber optic image bundle and the second supporting means, permits the fused fiber optic image bundle to expand, twist or move during deflection and usage of the endoscope and permits relative movement to occur without damaging or otherwise breaking the fused fiber optic image bundle. Such a supporting means would not be required if a flexible, centrally etched fiber optic image transmitting bundle were used.

Another advantage of the present invention is that a fused fiber optic image bundle can be rigidly attached at its proximal end to the second supporting means and slidably supported at its distal end by a first supporting means which permits relative movement between the fused fiber optic image bundle and the instrument to occur at the distal end of the fused fiber optic image bundle. In this structure, an adjusting means is provided for applying an axial translational force to the fused fiber optic image bundle to move the entire bundle in a selected direction so as to focus the image from an objective lens located at the distal end of the instrument onto the face of the fused fiber optic bundle so that a viewable image can be viewed through the proximal end of the fused fiber optic image bundle.

Another advantage of the present invention is that an adjustable ocular power correcting lens or other similar means can be utilized to provide a means for focusing the viewable optical image by the user for diopter correction at the proximal end of the endoscope.

Another advantage of the present invention is that a method for casting a housing around an endoscope frame is shown. In the preferred embodiment, the method includes the step of assembling an endoscope frame such that the working channels, the fused fiber optic image bundle channel and the fiber optic light carrying means are positioned in a pre-determined arrangement, all of which continue beyond the proximal end of the elongated shaft. Each of the above elements are located to extend from the housing at preselected locations relative to a predetermined exterior outer surface of the housing cast around the endoscope frame and elements forming a liquid tight seal therebetween. The input opening means or port of the working channels and the light connecting means or light post for the fiber optic light carrying means extends a preselected distance beyond the exterior surface of the housing so the same are accessible to a user.

Another advantage of the present invention is that the method for casting a housing around the endoscope frame includes the step of forming a mold having a cavity of a predetermined shape which defines the predetermined exterior outer surface and shape of the housing and defines the openings within the housing for passing the input opening means for the working channels, the light connecting means or light post for the fiber optic light carrying means to extend through the housing and a viewing means within a viewing opening for the user to view a viewable image from the fiber optic image bundle.

BRIEF DESCRIPTION OF THE DRAWING

These and other advantages of the invention will be readily apparent when considered in light of the detailed description hereinafter of the preferred embodiment and of the drawing which include the following figures:

FIG. 1 is a top and front perspective view of a endoscope shaft assembly having a cast housing and an elongated shaft having a distal end which terminates in a triangular shaped cross-sectional distal tip;

FIG. 2 is a top and rear perspective view of the endoscope shaft assembly of FIG. 1;

FIG. 3 is a partial top and front perspective view of the endoscope shaft assembly showing the light connecting means which is operatively connected to the fiber optic light carrying means;

FIG. 4 is a partial top and rear perspective view of the endoscope showing the input opening means or ports to a 3.4 French working channel and to a 2.3 French working channel;

FIG. 5 is a top plan view thereof;
FIG. 6 is a front elevational plan view thereof;
FIG. 7 is a bottom plan view thereof;
FIG. 8 is a left side elevational view thereof;
FIG. 9 is a right side elevational view thereof.

Figure 12:
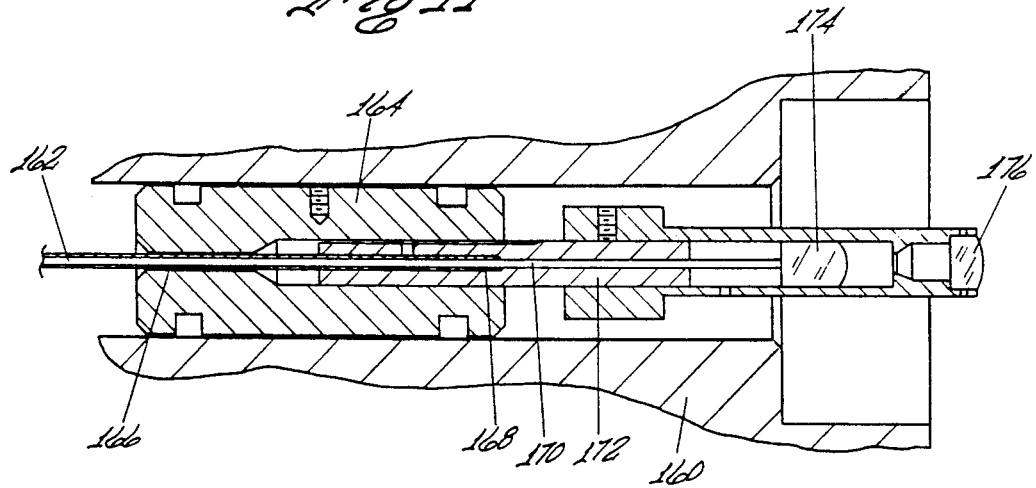
Figure 13:
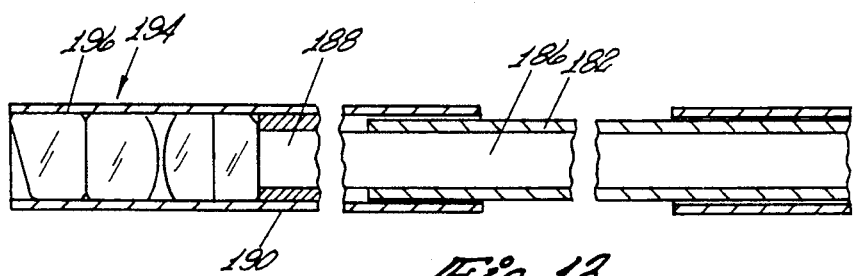
Figure 15:
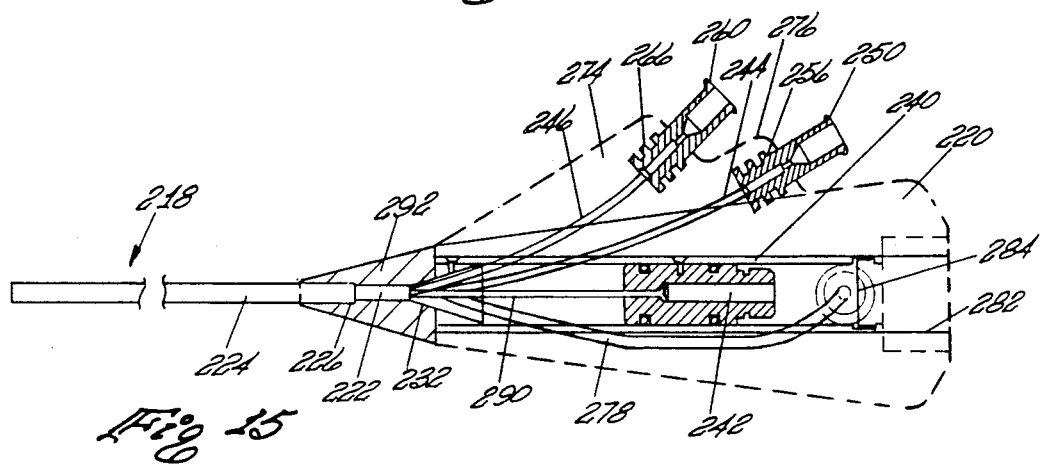
Figure 14:
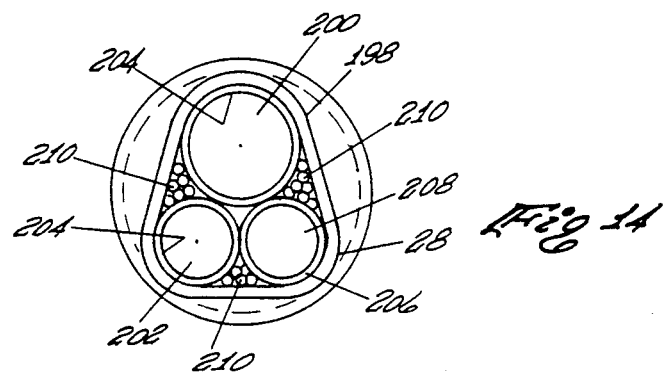
Figure 16:
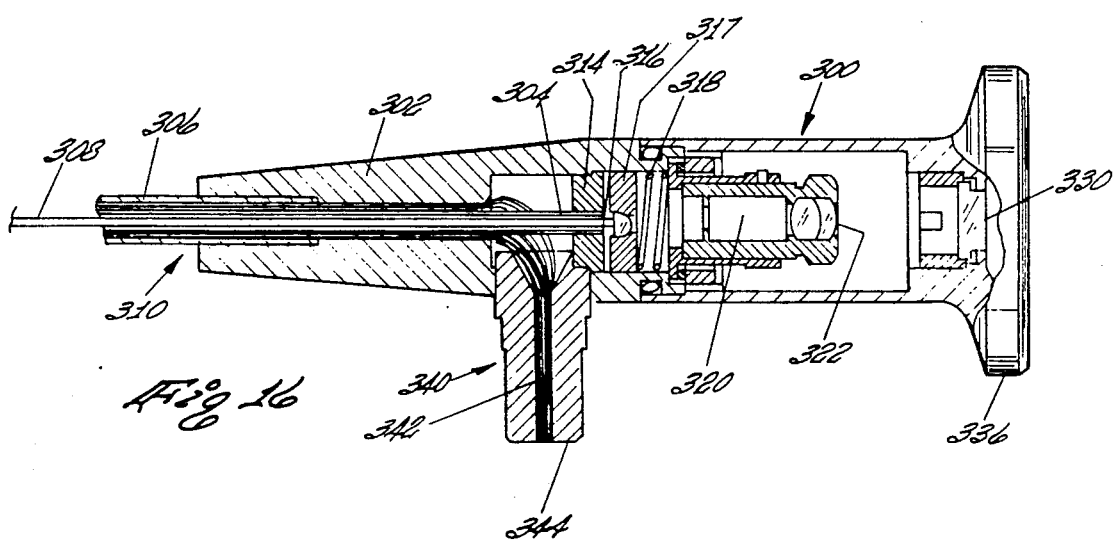

FIG. is a pictorial representation of yet another embodiment of a fiber optic imaging means for an instrument wherein the fused fiber optic image bundle proximal end is rigidly affixed to a second supporting means;

FIG. 12 is a partial cross-sectional representation of yet another embodiment of an endoscope for providing a second supporting means which has the distal end of a fused fiber optic image bundle rigidly affixed to first support means and includes means for permitting the fused fiber optic image bundle to move at its proximal end;

FIG. 13 is a pictorial representation of the relationship of the objective lens relative to the face of the fused fiber optic image bundle located at the distal end and the use of an optical wedge lens to establish the angle of view;

FIG. 14 is a front elevational view of the distal tip which terminates in a triangular shaped distal tip having a first working channel, a second working channel, a fiber optic image bundle channel, a fused fiber optic image bundle within the fiber optic image bundle channel and the fiber optic light carrying means interspersed around the channels, all of which are located within the interior of the first elongated sheath tube;

FIG. 15 is a pictorial representation of a cast housing showing the relationship between the endoscope frame, the input means for each of the working channels, the light connecting means for the fiber optic light carrying means and the bulkhead support means for slidably supporting the image viewing means; and FIG. 16 is a pictorial representation of yet another embodiment of a rigid endoscope utilizing the teachings of this invention.

DESCRIPTION OF THE PREFERRED EMBODIMENT

FIGS. 1-9 and FIG. 12 illustrate an endoscope for practicing this invention. The preferred embodiment of the endoscope illustrated in FIGS. 1-9 and FIG. 12 is as a mini-rigid ureteroscope. The mini-rigid ureteroscope permits direct visualization of the ureter for diagnostic, therapeutic and endoscopic applications. In performing such procedures, the geometrical dimension of the ureteroscope and the flexibility of the distal end are important factors to the urologist utilizing the same. Typically, the size of the instrument, including its distal tip, is measured in the units referred to as "French". For purposes of this application, the following formula is utilized to designate the geometrical dimension in the French units:

(1) Profile of tip in millimeters (around the periphery of instrument) / $\pi$ = Equivalent diameter (2) Equivalent diameter * 3 = French (unit)

For example, if the instrument has a circular cross-sectional circumference or perimeter of about 3.14 millimeters, the equivalent diameter would be about 1 millimeter. Thus, multiplying the equivalent diameter of 1 millimeter times a factor of 3, the size of the instrument would be equal to 3 French.

In the present application, the French units are utilized to describe the size of the shaft and working channels, it being understood that the measurement is made as a function of the periphery of the device defined in French units using the above formula. Thus, whether the cross-sectional area of an elongated sheath tube is circular, a non-circular, such as triangular shaped, tear drop shaped, elliptical shaped or other geometrical shape, by utilizing the above formula, the size can be converted to a standard French unit for comparison purposes.

It is known to a person skilled in the art to utilize the French unit as the method of measuring the size of the endoscopic instrument. For purposes of explanation herein, this terminology is used herein. However, by using the French units of measurement, it is not intended to limit the scope of the disclosure or invention because of the method of explanation.

FIGS. 1-9 and FIG. 12 disclose a mini-rigid ureteroscope, shown generally as 20. This mini-rigid ureteroscope is only one of many variations of endoscopes or instruments that can be fabricated using the teachings of the present invention. In the embodiment of FIGS. 1-9 and FIG. 12, the endoscope includes an elongated shaft, shown generally as 22. The elongated shaft includes a first elongated sheath tube, shown generally as 26, which includes a deflectable distal section 28 and a blended section 36 which extends to the proximal section of the first elongated sheath tube 26. The first elongated sheath tube 26 has, at its distal end, a triangular-shaped cross-sectional area of a selected geometrical dimension which terminates in a distal tip 32. It is envisioned that the distal section would terminate in other than a triangular-shaped cross-sectional area. Any non-circular cross-sectional area or a geometrically shaped cross-sectional area having at least one protuberance can be used. For example, the geometrical shape can be tear drop shaped, elliptical shaped, rounded rectangular shaped or the like.

The second semi-rigid elongated sheath tube 34, has a predetermined length which is greater than one-half of the selected length and less than the selected length. This places the transition zone 38 of the two sheaths near the distal tip. The second semi-rigid elongated sheath tube 34 is positioned over, encloses and supports the proximal section of the first elongated sheath tube 26 with the deflectable distal section 28 extending beyond the second semi-rigid elongated sheath tube 34. The second elongated sheath tube 34 has a cross-sectional shape sufficient to pass the first elongated sheath 26 therethrough.

As is evident from the FIGS. 1 and 2, specifically, the first elongated sheath tube 26 and a second elongated sheath tube 34 are coaxially aligned tubes and the proximal section of the first elongated sheath tube 26 extends at least to the proximal end of the second semi-rigid elongated sheath tube 34. In the preferred embodiment, and as discussed further in connection with FIG. 14, the proximal end of the first elongated sheath tube 26 extends beyond the proximal end of the second semi-rigid elongated sheath tube 34. In order to provide redundant fastening, the proximal end of the first elongated sheath tube 26 is flared to be embedded within a cast housing as described in connection with FIG. 14 hereinbelow.

FIGS. 1 and 2 also show that the deflectable distal section 26 blends at area 36 into an inner section 30 spaced from the distal tip 32. The inner section 30 is essentially in the form of a continuation of the first elongated sheath tube 26 and has, in the preferred embodiment, a generally circular cross-section which blends or tapers from the circular cross-section to the triangular cross-section at area 36, and wherein the triangular shaped cross-sectional area terminates at the distal tip 32. The transition zone between the second semi-rigid elongated sheath tube and the deflectable distal section is shown as 38. At the distal end of the second semi-rigid elongated sheath tube, the end is tapered mechanically by polishing or other known manufacturing procedure.

The proximal end of the first elongated sheath tube 26 and a second semi-rigid elongated sheath 34 is operatively connected to a housing shown generally as 40. In the preferred embodiment, the housing 40 comprises a cast housing 42 having a predetermined shape and an exterior outer surface and which includes openings therein to permit passage of certain of the various functional elements as working channels of the endoscope, therethrough as will be explained in connection with the description of FIG. 14 hereinbelow. The endoscope 20 includes a first working channel, a second working channel, a fused fiber optic image bundle channel and a fiber optic light carrying means wherein the fiber optic light carrying means is generally interspersed around the working channel and fused fiber optic image bundle channel, all of which are located within the interior of the first elongated sheath tube 26.

The housing 40 includes means for continuing each of the working channels, the fused fiber optic image bundle and the fiber optic light carrying means to a location external to the exterior outer surface of the housing 42. Further, the housing 42 provides a rigid support for the input opening means of the working channels and the light connection means for the fiber optic light carrying means as described below.

The first working channel terminates in an input opening means or port 48, which is operatively connected to the first working channel which, in the preferred embodiment, has a measurement of 3.4 French. The input opening means or port 48 is supported by a shoulder member 44 which extends laterally from the housing 42. The second working channel terminates in a separate input opening means or port 50 and, in the preferred embodiment, the second working channel has a measurement of 2.3 French. The input opening means or port 50 is supported by a shoulder 46 which extends laterally from the housing 42.

As is illustrated in FIGS. 1–5 and 7, the relationship of the shoulders 44 and 46 is such that the ports 48 and 50, respectfully, are positioned at predetermined relationships to each other and to the housing 42 to enable the urologist or user to easily access each of the working channels through ports 48 and 50, particularly when the endoscope 22 is positioned in a patient. Also, in the preferred embodiment, both parts are located in the same side for ease of access.

The housing 42 includes means for supporting a light post 54 which is a light connecting means which is operatively connected to the fiber optic light carrying means. The light post 54 is adapted to be operatively connected to a fiber optic light carrying means or light guide means which, in turn, receive light from a light source.

The housing 42 includes viewing means for supporting a lens system, shown generally a 60, and an adjustable ocular lens system 62 for diopter correction to permit a surgeon to view the optical image which is transmitted axially along the endoscope. The fiber optic image bundle terminates in a lens system which transmits a viewable image to the objective lens. This is described in greater detail in connection with FIGS. 5, 10 and 11.

In addition, the housing 42 includes indented, formed support surface 64 which is formed into the housing 42 to permit the urologist or user to grasp and support the mini-rigid ureteroscope 22 in order to advance, rotate and maneuver the same with a firm positive grasping relationship between the instrument and the hand of the user.

In use, the distal section 28 has a size of about 7 French which allows the endoscope to be passed into the undilated ureter of a patient. The two working channels, having ports 48 and 50, permit simultaneous irrigation and passage of working instrument, accessories and the like. In the preferred embodiment, the mini-rigid ureteroscope 20 can have two working lengths such as, for example, a 33 centimeter length and a 41 centimeter length. The shorter length may be used for distal ureteroscopy and the longer unit may be used in the proximal ureter and renal pelvis.

The two accessory ports 48 and 50 are selected to have a sufficient size to permit passage of accessories having a size of approximately 3 French which could be utilized in the 3.4 French working channel and accessories having a size of approximately 2 French would permit passage of accessories having a size of approximately 2.3 French. As is explained in the connection with the description of FIG. 5, the interior walls of each channel can be coated with a material which has a slippery characteristic or low coefficient of friction such that the accessories can be easily transported within the channel. As such, a procedure can be performed with a minimum of sliding friction existing between the accessories and the interior of the working channels. Accessories which could be utilized in the working channel include, without limitation, flexible accessories such as stone baskets, retrievers, forceps, electrohydraulic lithotriptor probes and laser fibers. Also, the channel may be used for irrigation and suction.

In the preferred embodiment, and as further discussed in connection with FIGS. 10, 11 and 13 hereof, an optical wedge can be utilized in conjunction with the objective lens at the distal tip of the first elongated sheath tube 26 to provide an angle of view. In the preferred embodiment, the view can be about 5 degrees to about 10 degrees. By selecting an appropriate angle of view, the urologist can quickly visualize the accessory device as it exits the distal tip of the working channel. Of course, the angle of view could vary as to the type of media. For example, the effect of the optical wedge would be that if the direction of view in water is about 5 degrees, then the direction of view in air would be about 14 degrees. The reason for this difference is directly a function of the index of refraction of the medium in which the optical image is being viewed.

In the preferred embodiment as illustrated in FIGS. 1-9, the following endoscope specification ranges would apply:

ENDOSCOPE SPECIFICATION RANGES

1. Shaft diameter:
   Tip = 6 Fr −8 Fr for 1 cm −7 cm
   Middle = 8 Fr −9 Fr for 5 cm − 10 cm
   Proximal = 9 Fr −11 Fr
2. Working channel: 2 Fr-3 Fr (positioned on outside)
3. Working channel: 3 Fr-4 Fr (positioned on inside)
4. Working length: 30 cm-45 cm
5. Overall length: 40 cm-60 cm
6. Direction of view: 0°-10°
7. Field of view: 60°-85°
8. Depth of field: 2-40 mm 9. Diopter correction: preferred With respect to use of the endoscope as a mini-rigid ureteroscope as described hereinbefore, the following are two examples of specific mini-rigid ureteroscopes utilizing the teachings of the preferred embodiment of the invention as described herein:

|  | EXAMPLE I | EXAMPLE II |
|---|---|---|
| Sheath length/diameter (measured from the distal end) | | |
| Distal: | 4.5 cm/6.9 Fr | 4.5 cm/6.9 Fr |
| Middle: | 5.5 cm/8.3 Fr | 5.5 cm/8.3 Fr |
| Proximal: | 23 cm/10.2 Fr | 31 cm/10.2 Fr |
| Total working length: | 33 cm (13.0") | 41 cm/(16.2") |
| Overall length: | 49 cm (19.3") | 57 cm (22.4") |
| Weight: | 5.6 ounces | 5.7 ounces |
| Working Channels (2): | 3.4 Fr and 2.3 Fr | 3.4 Fr and 2.3 Fr |
| Field of view: | 70° | 70° |
| Angle of view: | 5° | 5° |
| Depth of focus: | 2-40 mm | 2-40 mm |

In order to measure the deflection of the deflectable distal end, the following tests were conducted on the mini-rigid ureteroscopes of Example I and II.

The housing 42 of the mini-rigid ureteroscope was clamped on a clamping surface with the 3.4 French working channel positioned vertically placing the base of the triangular shaped distal end essentially horizontal to the clamping surface. A downward force of 295 grams was applied ¼ inch in from the distal tip. The following deflections were measured at the distal tip:

|  | EXAMPLE I | EXAMPLE II |
|---|---|---|
| Deflections at end of shaft (295 grams) | 4.3 cm | 7.9 cm |

Figure 10:
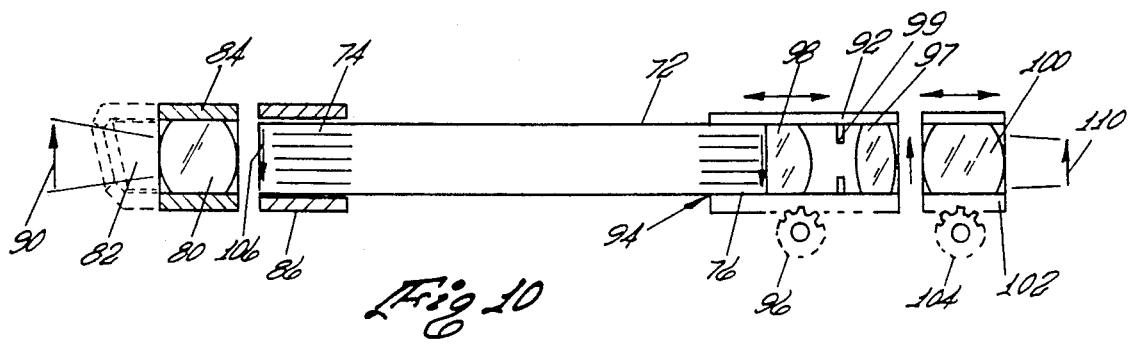
FIG. 10 is a pictorial representation of a fiber optic imaging means for an instrument having a fused fiber optic image bundle wherein the proximal end of the fiber optic image bundle is rigidly affixed to a second supporting means and the proximal end is slidably mounted in a second supporting means.
Figure 11:
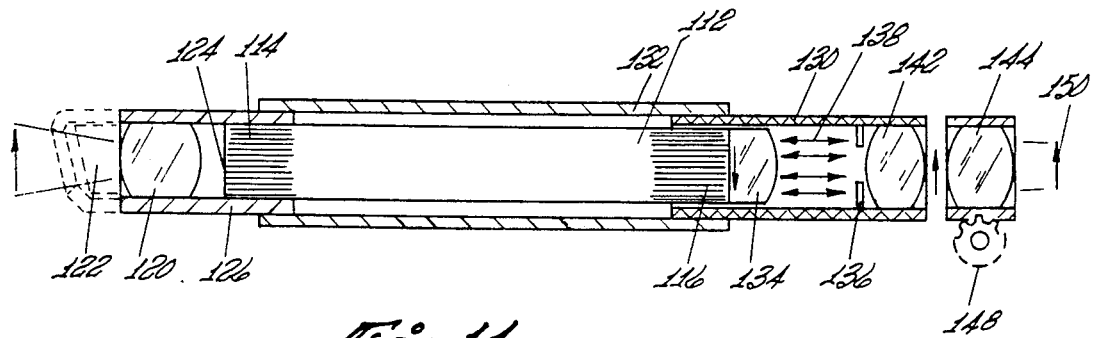

FIGS. 10 and 11 depict pictorially two different lens systems that may be utilized using a rod-like image transferring means such as, for example, fused fiber optic image bundle for producing a viewable image at the proximal end of the endoscope or instrument.

In FIGS. 10, the fused fiber optic image bundle 72, which in the preferred embodiment, is a coherent, cane-like fused fiber optic image bundle having a plurality of separate fiber optic elements which are joined together, is utilized as the fiber optic image bundle. However, it is readily apparent to a person skilled in the art that the rod-like image transferring means could be a GRIN lens system or the like. The term "rod-like image transferring means" is intended to cover the use of a cane-like coherent fiber optic image bundle, an etched, coherent fiber optic image bundle (wherein each of the fiber optic elements are independent and are movable relative to each fiber optic element), a GRIN lens or other similar lens system.

In FIG. 10, the fiber optic image bundle 72 has a distal end 74 and a proximal end 76. The distal end 74 is positioned at a predetermined space from an objective lens 80 supported by lens support 84. If desired, an optical wedge, shown by optical wedge 82 and a support, both being shown in dashed lines, can be utilized to direct the field of view to some preferred direction in the objective field. In the embodiment of FIG. 10, the distal end 74 of the fiber optic image bundle 72 is movable relative to the objective lens 80. A first support 86 is slidable connected to the distal end 74 to permit relative movement therebetween. The object being viewed through the objective lens 84 is shown by arrow 90.

The proximal end 76 of the fiber optic image bundle 72 is supported by and is rigidly affixed to a second support means 92. The support means 92 includes an aperture stop 99 and an objective lens 97. The proximal end 76 can be operatively connected to the second support means 92 by means of any one of several means, such as for example, the use of an epoxy bond at the common surface shown generally as 94.

The second support means 90 is operatively coupled to a drive member 96 which is capable of applying an axial translational force to the fused fiber optic image bundle 72 so as to move the same in a selected distance, i.e. either towards or away from the objective lens 80, such that the image of object 90 passed by the objective lens 80 is focused onto the face 106 of the distal end 74 of the fused fiber optic image bundle 72.

The second support means 92 includes a field lens or an objective lens 98 which forms a viewable image from the virtual image transmitted by the fiber optic image bundle 72. The focused image from the field lens 98 is passed through an adjustable ocular power correction lens 100 which is supported in position by a lens support 102. The lens support 102 is operatively connected to an adjusting mechanism 104. The adjustment mechanism 104 can be adjusted to move the ocular lens 100 axially relative to the fiber optic image bundle 72 axis to provide a focusable viewable image to a viewer to correct for diopter variations, which focusable image (which would occur in the eye) is depicted by arrow 110.

FIG. 11 shows another embodiment of a fused fiber optic imaging means for an instrument. A means defining a fiber optic image bundle channel such as, for example, channel 132, supports a fiber optic image bundle 112 centrally thereof. The means for defining a fiber optic image bundle 112 has a distal end 114 and a proximal end 116 for transmitting an optical image within the instrument. The fused fiber optic image bundle 112 is located within the fiber optic image bundle channel 132 such that the distal end 114 of the fiber optic image bundle 112 is located at one end of the instrument and the proximal end 116 of the fiber optic image bundle 112 is located at the opposed second end of the instrument.

In FIG. 11, a means for defining an objective lens 120 at the one end of the instrument, the objective lens 120 which is spaced from the distal end 114 of the fused fiber optic image bundle 112 for focusing an optical image into the face 124 of the fused fiber optic image bundle 112 at the distal end thereof. An optical wedge 122 and support, shown by dashed lines, establish the direction of the field of view.

A first supporting means at the distal end 114 and shown generally as 126, is operatively connected between the fused fiber optic image bundle channel 132 and the distal end 114 of the fused fiber optic image bundle 112 for supporting the distal end 114 of the fused fiber optic image bundle 112 within the instrument. In the embodiment of FIG. 11, the first supporting means likewise functions as a means for supporting the objective lens 120. By utilizing the first supporting means 126 to rigidly fix the position of the objective lens 120 at a predetermined distance from the face 124 of the distal end 114 of the fused fiber optic image bundle 112, objects within the depth of focus of the objective lens 120 are always focused onto the face 124 of the distal end 114 of the fiber optic image bundle 112.

The proximal end 116 of the fused fiber optic image bundle 112 is supported by a second supporting means 130 Which is slidably operatively connected thereto for permitting the proximal end 116 of the fiber optic image bundle 112 to move relative to the instrument. An field lens 134 is operatively connected to the distal end 116 of the fiber optic image bundle 112.

The second supporting means 130 includes a cavity which permits the image to be passed therethrough and through an aperture stop 136 to an objective lens 142 positioned axially along and spaced from the field lens 134. An adjustable focus ocular lens 144 is positioned a predetermined distance from the objective lens 142 for enabling a viewer to focus the viewable optical image received from the objective lens 142. The adjustable ocular power correcting lens 144 is supported by a lens support 146 which is adjustable by means of an adjusting means 148. The adjusting means is operable to move the adjustable focus ocular lens 144 axially relative to the axis of the objective lens 142 to enable a viewer to focus, for diopter correction, a viewable image which is depicted by arrow 150.

With respect to the preferred embodiment described in FIGS. 1-9 hereof, the lens system illustrated pictorially and discussed in connection with FIG. 11 and is shown in detail in FIG. 12 is the preferred lens system. However, it is envisioned that the lens system of FIG. 10 could likewise be used in the preferred embodiment illustrated in FIGS. 1-9.

FIG. 12 depicts the preferred embodiment of the proximal portion of the fused fiber optic imaging means of an endoscope wherein the endoscope contains a fiber optic image bundle channel 162 which encloses a fused fiber optic image bundle 170. The elongated shaft (which can be of a structure as illustrated in connection with FIGS. 1-9), encloses the fiber optic image bundle channel and fiber optic image bundle. Of importance is that FIG. 12 illustrates the means wherein the fused fiber optic image bundle channel 162 passes through and is supported by a support means 164 in housing 160 through a slidable support slot shown as 166. The fiber optic image bundle channel is shown terminating at a proximal end 168. The fused fiber optic image bundle 170 is then passed through a support member 172 which is slidably supported in support means 164. Field lens 174 is optically bonded to the proximal end face of the fused fiber optic image bundle 170. A proximal objective lens 176 is mounted into housing 178 which in turn is rigidly affixed to support member 172. A proximally located ocular lens (not shown) is used to magnify the image created by the proximal objective lens 176 for operator viewing.

FIG. 13 illustrates pictorially a preferred embodiment for terminating the distal end of an endoscope utilized as a mini-rigid ureteroscope. In FIG. 13, a fiber optic image bundle channel 182 supports a fused fiber optic image bundle 186. The first supporting means 190 supports the distal end 188 of the fused fiber optic image bundle 186. Concurrently, the first supporting means 190 supports an objective lens system, shown generally as 194 which includes an optical wedge 196, in a fixed spaced relationship to the distal end 188 of the fused fiber optic image bundle 186.

The lens system of FIG. 13 can be utilized in a wide variety of endoscopes including specifically the mini-rigid ureteroscope depicted by FIGS. 1-9 and FIG. 12 hereof.

A mini-rigid ureteroscope utilizing the teachings of the present invention has a triangular shaped cross-sectional area of a selected dimension which terminates in a distal tip. FIG. 14, illustrates, in an end elevational view, the structure of an endoscope which is utilized as a mini-rigid ureteroscope depicted in FIGS. 1-9. In FIGS. 1-9, the first elongated sheath tube 26 terminates in a triangular shaped Cross-sectional member 28 having a triangular shaped periphery shown by thin walled member 198 which defines an outer peripheral surface. The length of the outer peripheral surface of thin-walled member 198 is used to calculate the French size of the instrument at the distal end as described hereinbefore. The triangular shaped distal tip 28 encloses all of the functional working elements which are located interiorly to the first elongated sheath tube 26.

In FIG. 14, the triangular shaped distal end 28, which is defined by the thin walled member 198, encloses at lease one working channel and, in the preferred embodiment, encloses a first working channel 200 in and a second working channel 202. As depicted in FIG. 14, the working channels are of different sizes. However, it is also envisioned that an endoscope could utilize a first working channel and a second working channel of the same size. In the embodiment illustrated in FIG. 14, the larger working channel 200, has the size of 3.2 French while the second working channel, channel 202, has a working size of 2.3 French.

Since working tools, accessories and the like can be utilized in each of the working channels 200 and 202, the interior walls of each of the working channels can be coated or formed with a coating material depicted by surface 204, which has a low coefficient of sliding friction to reduce the amount of sliding friction between a working tool or an accessory utilized in the channel and the walls defining the working channel.

In FIG. 14, a fiber optic image channel 206 includes a fiber optic image bundle 208. During fabrication of the endoscope, the fiber optic image bundle 208 need not be inserted into the fiber optic image bundle channel 206 until final assembly of the endoscope. This is important in connection with the method of casting the housing, which is described hereinafter, with respect to FIG. 15.

In addition, in order to provide sufficient light to the viewing area on site located adjacent the distal tip of the instrument in a cavity or passageway, a fiber optic light carrying means, such as, for example, the fiber optic elements shown generally as 210, are interspersed around the first working channel 200, the second working channel 202 and the fiber optic image bundle channel 206. If an optical wedge is utilized, such as for example, optical wedge depicted as 196 in FIG. 13, the optical wedge would be positioned an axial alignment with the face of the fiber optic image bundle 208 illustrated in FIG. 14 and oriented so that the viewing angle is directed towards the working channels.

FIG. 15 illustrates pictorially a method for casting a housing around an endoscope frame. In FIG. 15, the elongated shaft, shown generally as 220, includes a first elongated sheath tube 222 having a proximal end which terminates in a flared end 232. A second semirigid elongated sheath tube 224 has its proximal end 226 which terminates a predetermined distance before the flared end 232 at the first elongated sheath tube 222. The generally circular shaped proximal end 226 has a generally cross-sectional area which is of a sufficient geometrical dimension to permit the proximal section of the first elongated shaft 222 to pass therethrough.

The housing 220 including its endoscope frame 240 is depicted in FIG. 15 and includes means for continuing a first working channel 244 which terminates in an input opening means, or port 250. Port 250 includes a serrated bottom support member 256. The input opening means, or port 250 is operatively connected to the first working channel which, in the preferred embodiment, has a size of 3.4 French. The housing 220 includes a first shoulder 276 which is adapted to support and position the serrated bottom member 256 of the input opening means or port 250 securely within the housing 220.

In addition, the housing 220 and its endoscope frame 240 includes means for continuing a second working channel 246 which terminates in an input opening means or port 260. In the preferred embodiment, the second working channel, which terminates in port 260, having a size of 2.3 French. Input opening means or port 260 includes a serrated support bottom member 266 which is positioned in and is supported by a shoulder 274 which is part of and is defined by the housing 220. The ports 250 and 260 are positioned in a relationship to each other end to extend in a selected direction from the housing 220 so as to permit a urologist or user to have access to each of the working channels. The ports 250 and 260 could be located in other positions around the housing, for example, one on each side of the housing.

In addition, the interior portion of the housing 220 encloses the endoscope frame 240 which is adapted to form a part of the structure of the housing 220 and include a bulkhead means 242 for supporting a viewing means which is adapted to cooperate with a fused fiber optic image bundle which is ultimately to be located into the fiber optic image bundle channel as shown in FIG. 14. In the housing illustrated in FIG. 15, the fused fiber optic image bundle assembly has not been installed into the assembly.

In addition, a fiber optic light carrying means 278 extends from the proximal end of the endoscope through the flared end 232 of the first elongated sheath tube 222 and extends up to a light input connecting means or light post 284. The housing 220 further includes means for defining an opening or aperture 282 which is in coaxial alignment with the bulkhead means 242. The aperture 282 is used in the preferred embodiment to receive and support an ocular lens as shown in element 62 in FIGS. 1-9.

In order to fabricate the housing and assembly described in FIG. 15, a unique and novel method for casting housing around an endoscope frame is utilized in fabricating the preferred embodiment of the invention. The method for casting a housing around an endoscope frame comprises assembling an endoscope frame 240 which includes the proximal end of an elongated shaft and specifically includes the flared end 232 of the first elongated sheath tube 222. In the embodiment of FIG. 15, the elongated shaft includes a first working channel, a second working channel and a fiber optic light carrying means which are continued with the housing 220. In FIG. 15, the continuation of the first working channel is shown as element 244, the second working channel is shown by element 246 and, the fiber optic image bundle channel 290 is adapted to cooperate with a bulkhead means 242. The fiber optic light carrying means is depicted by element 278 and terminates in the light input means or light post 284. As such, each of the working channels and the fiber optic light carrying means terminations extend in separate and distinct predetermined directions from the elongated shaft to a preselected location through the housing 220 and then extend beyond the exterior outer surface of housing 220. Each of the working channels are terminated in an input opening means, namely input opening means 250 and 260 which extend beyond the housing 220. The fiber optic image bundle cooperates with a bulkhead means 242 which is interior to the housing 220 and in central opening 282.

When the endoscope frame has been assembled, as described above, the next step comprises casting with a curable material a housing wherein the housing is formed around the endoscope frame and has a predetermined shape and an exterior outer surface. As such, the casting material encloses and surrounds the proximal end of the elongated shaft, including the flared end 232, encloses the means continuing the first working channel 244 and the second working channel 246, the fiber optic image bundle channel 290 and the fiber optic light carrying means 278 such that the input opening means 250 and 260 of each of the working channels 244 and 246, respectively, extend through the exterior outer surface of the housing 220 at separate and distinct locations while being located in a special relationship from the exterior outer surface. The bulkhead means 242 is positioned centrally within the housing within the interior of the opening 282. The housing 220 forms a light tight fluid seal between the housing and each of the above described elements.

In connection with the above method, as described hereinbefore, the elongated shaft, namely the first elongated sheath tube 222, has an outer surface which engages the rear section 292 of the housing 220. During the step of casting, the casting would include the step of enclosing the flared end 232 of the elongated shaft 218 in a casting material defining the rear section 292 of housing 220 to form a redundant fastening of the elongated shaft 218 to the cast housing 220. The redundant fastening comprises a mechanical interface between the flared end 232 of the elongated shaft 218 and a cast housing 220 while a second fastening occurs through the gripping action between the outer surface of the proximal section of the elongated shaft, namely proximal end of the first elongated sheath tube 222 operatively connected to the flared end 232 and the proximal section of the second semi-rigid elongated sheath tube 224 including proximal end 226 and the rear section 292 of the housing.

The shape and exterior outer surface of the housing 220 including its rear section 292 is formed from a mold having a cavity which defines the predetermined shape and exterior outer surface. The mold includes openings to support the input opening means of each of the working channels and the light connecting means, or light post, of the fiber optic light carrying means.

The next step of the method utilizing the mold would be positioning the mold around the endoscope frame 240. After the endoscope frame 240 is in place and the other functional elements are in the proper openings in the mold, the mold is then filled with a curable casting material. The cast material can be any well known casting material such as for example a two part polyurethane material system which includes a polyurethane resin and appropriate hardener. During the curing of the casting material in the mold in the presence of the endoscope frame, the assembly may be placed, during the curing process, into a baking oven. It is important that, during the curing process, the overall temperature of the assembly of the mold, casting material and endoscope frame and the functional components do not exceed a temperature which would affect the mechanical characteristics of the working channels, the fiber optic image bundle channel and the fiber optic light carrying means. If a curing material is utilized which produces an exothermic reaction, and the same occurs at room temperature or in the alternative the curing takes place in a controlled atmosphere, such as, for example, a baking oven at 80° C. (176° F.), the curing temperature and/or baking temperature must be limited to a temperature would not affect the mechanical characteristics of the functional elements as described above.

It is envisioned that any type of casting material could be utilized, such as a curable polymer plastic, polyurethane material or any other material which could by utilized for an acceptable housing for an endoscope or for a mini-rigid ureteroscope.

When the curing process is completed, the next step would be removing of the mold when the casting material is cured.

FIG. 16 depicts yet another embodiment utilizing the teachings of this invention for a rigid endoscope 300. A housing 302 supports a first elongated sheath tube 304 which is enclosed by a second semirigid elongated sheath tube 306. A fused fiber optic image bundle 308 would extend centrally through the elongated shaft 310 defined by the first elongated sheath tube 304 and the second semi-rigid elongated sheath tube 306.

The fused fiber optic image bundle 308 would terminate at a proximal end 316 in a support member shown generally as 314 which would be in the form of a slidable supporting means for the proximal end 316 within the housing 302. A lens support 317 cooperates with a spring means 318 to permit relative movement between the fused fiber optic image bundle 308 and the housing 302. The optical image which would be located at the proximal end 316 of the fused fiber optic image bundle 308 which is viewed through ocular lens system 322. A window 330 is provided in the eyepiece 336. A fiber optic light carrying bundle, shown generally as 342, would extend from the distal end of the endoscope, interspersed between the first elongated sheath tube 304 and the second elongated sheath tube 306 and into a light post structure 340 having a support boss 344 for providing a connecting means between a light guide and a light source.

The teachings set forth herein are directed in the preferred embodiment to medical applications. However, the teachings hereof could be used in other applications, such as, for example, borescopes, industrial systems, nuclear systems and the like. All such applications are envisioned to be encompassed by the apparatus and methods disclosed and claimed herein.

What is claimed is:

1. A method for casting a housing around an endoscope frame comprising casting with a curable material a housing having a predetermined shape and exterior outer surface around an endoscope frame including the proximal end of an elongated shaft, a first working channel, a second working channel, a fiber optic image bundle channel and a fiber optic light carrying means such that the input opening means of each working channel and a light connecting means of the fiber optic light carrying means extends through the exterior outer surface at separate and distinct locations which are positioned in a spaced relationship from the exterior outer surface and with a viewing means for the fiber optic image bundle positioned interiorly within said housing, all of which form a fluid tight seal with said housing.

2. A method for casting a housing around an endoscope frame comprising assembling an endoscope frame comprising a proximal end of an elongated shaft having a first working channel, a second working channel, a fiber optic image bundle channel, and fiber optic light carrying means which extends into and which is interspersed within the elongated shaft and around said first working channel, said second working channel and said fiber optic image bundle channel, each of said working channels and said fiber optic light carrying means extending in a predetermined direction from the elongated shaft to a preselected location wherein each of said working channels are terminated in an input opening means and wherein said fiber optic image bundle terminates in a viewing means, wherein said fiber optic light carrying means terminates in a light connecting means; and casting with a curable material a housing having a predetermined shape and exterior outer surface around an endoscope frame including the proximal end of an elongated shaft, a first working channel, a second working channel, a fiber optic image bundle channel and a fiber optic light carrying means such that the input opening means of each working channel and a light connecting means of the fiber optic light carrying means extends through the exterior outer surface at separate and distinct locations which are positioned in a spaced relationship from the exterior outer surface and with a viewing means for terminating the fiber optic image bundle being positioned interiorly within said housing, all of which form a fluid tight seal with said housing.

3. The method of claim 2 wherein the elongated shaft has a proximal section having an outer surface and wherein the proximal end includes a flared end and wherein the step of casting includes enclosing the flared end of said elongated shaft in the casting material to form a redundant fastening of the elongated shaft to the cast housing comprising a mechanical interface between the flared end of the elongated shaft and cast housing and a gripping interface between the outer surface of the proximal section of the elongated shaft and the cast housing.

4. The method of claim 2 further comprising the step of forming a mold having a cavity which defines a predetermined shape and external outer surface and wherein said mold includes openings to support the input opening means of each of the working channels, and the light connecting means of the fiber optic light carrying means.

5. The method of claim 4 further comprising the step of positioning the mold around said endoscope frame.

6. The method of claim 5 wherein the step of casting further comprises the step of filing the mold with a curable casting material.

7. The method of claim 6 further comprising the step of curing the casting material in the mold in the presence of the endoscope frame.

8. The method of claim 6 wherein the step of curing includes baking the assembly including the mold, curable material, endoscope frame.

9. The method of claim 8 wherein the step of casting further includes casting the housing wherein the curing process does not exceed a temperature which would affect the mechanical characteristics of the working channels and the fiber optic light carrying means.

10. The method of claim 8 wherein the step of casting includes using a casting material comprising a curable polymer.

11. The method of claim 9 wherein the step of casting includes using a casting material formed of a polyurethane resin and hardening agent.

12. The method of claim 7 further comprises the step of
   removing the mold when the casting material is cured.

13. The method of claim 2 further comprising the step of
   assembling an elongated shaft which is sufficiently rigid enabling it to be displaced through a ureter by axial and rotational translation by maneuvering of the shaft, said elongated shaft having a first elongated sheath tube having a semi-deflectable distal section and a proximal section and a second rigid elongated sheath tube which is slight shorter than said first elongated sheath tube and which is positioned contiguous to and encloses the proximal section of said first elongated sheath tube, said semi-deflectable distal section of said first elongated sheath tube terminating in a substantially triangular cross sectional distal tip which extends beyond said second elongated sheath tube a sufficient distance to be deflectable defining an elongated shaft having a generally smooth outer surface, said semi-deflectable distal section of said first elongated sheath tube being sufficiently flexible to be able to deflect as it enters into and dilates a ureter and said second rigid elongated sheath tube being sufficiently rigid to inhibit deflection.

* * * * *